United States Patent [19]

Hengartner et al.

[11] 3,972,898

[45] Aug. 3, 1976

[54] PROCESS FOR THE PREPARATION OF 6,6-ALKYLENEDIOXYALKAN-2-ONES

[75] Inventors: Urs Oskar Hengartner, Montclair; Pius Anton Wehrli, North Caldwell, both of N.J.

[73] Assignee: Hoffmann-La Roche Inc., Nutley, N.J.

[22] Filed: Mar. 20, 1975

[21] Appl. No.: 560,062

[52] U.S. Cl............................ 260/340.9; 260/397.4; 260/483
[51] Int. Cl.² .................................... C07D 317/26
[58] Field of Search.............. 260/340.9, 338, 340.7

[56] References Cited
UNITED STATES PATENTS

| | | | |
|---|---|---|---|
| 2,610,204 | 9/1952 | Moe et al............................ | 260/483 |
| 3,562,313 | 2/1971 | Cross et al........................ | 260/483 X |
| 3,567,744 | 3/1971 | Tanaka et al................ | 260/340.9 X |

FOREIGN PATENTS OR APPLICATIONS

| | | | |
|---|---|---|---|
| 4,535,548 | 11/1970 | Japan................................ | 260/340.9 |

*Primary Examiner*—Ethel G. Love
*Attorney, Agent, or Firm*—Samuel L. Welt; George M. Gould; Raymond R. Wittekind

[57] ABSTRACT

An improved process for the preparation of 6,6-alkylenedioxyalkan-2-ones starting from alkyl vinyl ketones and alkyl acetoacetates is disclosed. The 6,6-alkylenedioxyalkan-2-ones are useful as intermediates in the total synthesis of therapeutically valuable steroids.

15 Claims, No Drawings

PROCESS FOR THE PREPARATION OF 6,6-ALKYLENEDIOXYALKAN-2-ONES

BACKGROUND OF THE INVENTION

The commercial feasibility of processes for the preparation of medicinally valuable steroids depends, in the main, upon the availability and the cost of the starting materials. For example, in the synthesis of 19-norsteroids 3 described in U.S. Pat. No. 3,692,803, issued Sept. 9, 1972,

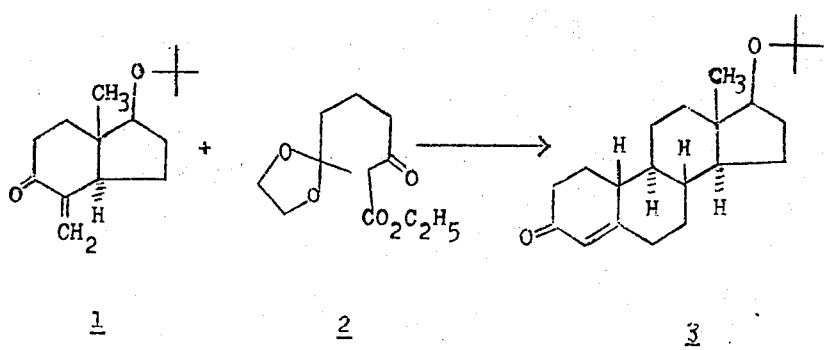

1   2   3 the commercial viability of the process depends upon the cost and availability of the bicyclic unsaturated ketone 1 and the ethylenedioxy-beta-ketoester 2, the starting materials. A process for the preparation of 6,6-methylenedioxyheptan-2-one 5, the precursor of the beta-ketoester 2,

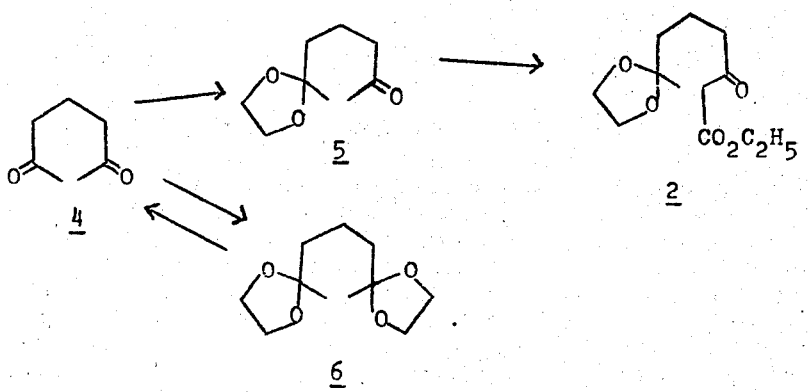

was disclosed in U.S. Pat. No. 3,767,677, issued Oct. 23, 1973. This process involved the ketalization of one of the two symmetrically situated keto groups of 4, and even though it was unexpectedly found that selective ketalization occurred in the presence of excess alkylene glycol, a minor amount of the diketal 6 was formed, in addition to the desired predominant monoketal 5. The formation of the diketal 6 necessitated a costly, inefficient and inconvenient separation step involving the formation of the bisulfite addition product of the monoketal 5, separation of the minor diketal 6 by extraction, hydrolysis of the bisulfite addition product to the major monoketal 5, hydrolysis of the diketal 6 to the dione 4 and recyclization of the dione 4 through the ketalization process. The economics of the process for the preparation of 7,7-ethylenedioxy-2-oxo octanoic acid ethyl ester 2 would be substantially improved and the availability of these steroid starting materials would be materially increased if a process for the preparation of the monoketal 5, eliminating the costly, inefficient and inconvenient bisulfite separation and recyclization steps of the process described in the aforementioned patent was available. The present invention describes a process which avoids the bisulfite separation and recyclization steps.

DETAILED DESCRIPTION OF THE INVENTION

The present invention relates to a novel, efficient and inexpensive process for the preparation of 6,6-alkylenedioxyalkan-2-ones. More particularly, the present invention relates to an efficient, commercially feasible method for the preparation of 6,6-alkylenedioxyalkan-2-ones comprising the steps of condensing a lower-alkyl vinyl ketone with a lower-alkyl acetoacetate to form a 3-lower-alkoxycarbonylalkan-2,6-dione, selectively ketalizing the 2-keto group to form a 3-lower-alkoxycarbonyl-6,6-alkylenedioxyalkan-2-one and saponifying and decarboxylating the 3-lower-alkoxycarbonyl group to form the desired 6,6-alkylenedioxyalkan-2-one.

As used throughout the specification and appended claims, the term "alkyl" denotes a straight or branched saturated hydrocarbon radical, such as methyl, ethyl, iso-propyl, tert.-butyl, hexyl, isooctyl and so forth and the term "lower" refers to the numerical range of 1 to 8.

In the formulas presented herein, substituents attached to the alkylenedioxy ring system may be in either the cis- or the trans- configuration, i.e., the substituents may be on the same side or on opposite sides of the average plane of the ring system. For example, the substituent designated $R_1$ may be in either the cis- or trans- configuration with respect to the spatial configuration of the substituent designated $R_2$ and the alkoxycarbonylalkanone side-chain.

Those compounds of the process of the present invention lacking an element of symmetry exist as optical antipodes and in the corresponding racemic forms. The present invention comprehends all possible optical isomers and racemic forms thereof. The formulas of the compounds of the process of the present invention shown herein are meant to include all possible isomeric and optical forms of the compounds depicted.

The process of the present invention for the preparation of 6,5-alkylenedioxyalkan-2-ones of formula 11 is illustrated in the Reaction Scheme.

In the first step of the process, an alkyl vinyl ketone of formula 7 is condensed with an alkyl acetoacetate of formula 8 to afford a 3-alkoxycarbonylalkan-2,6-dione of formula 9. The condensation reaction is generally performed in a lower-alkanol, such as methanol, ethanol or tert.-butanol containing a catalytic amount of the corresponding alkali metal alkoxide, such as sodium

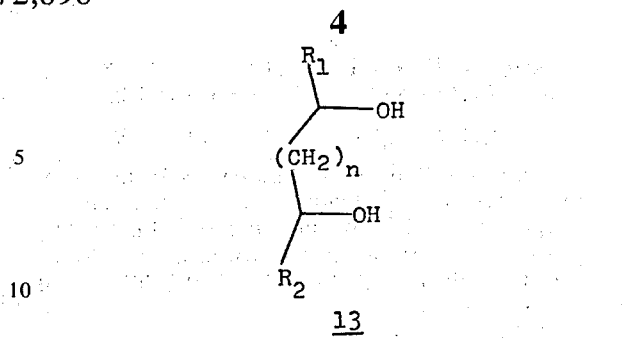

REACTION SCHEME wherein R, $R_1$ and $R_2$ are hydrogen or lower alkyl, $R_3$ is hydrogen or lower alkyl and $n$ is 0 to 2. or potassium methoxide, ethoxide or tert.-butoxide, at a reaction temperature of about 0° to about 30°C, employing about equimolar amounts of the reactants 7 and 8. A solution of about 2% sodium ethoxide in absolute ethanol is the preferred reaction medium and a temperature of about 20° to 25°C is the preferred reaction temperature. The relative molar amounts of the alkyl vinyl ketone 7 and the alkyl acetoacetate 8 are not critical. About equimolar amounts of the reactants 7 and 8 are preferred to avoid possible purification problems in subsequent steps.

A closely related procedure for the condensation of methyl vinyl ketone and ethyl acetoacetate was described in Chemische Berichte, 81, 197 (1948).

As reported in U.S. Pat. No. 3,767,677, treatment of heptan-2,6-dione with the requisite 3- to 6-molar excess of an alkylene glycol affords, in addition of a major amount of the desired monoketal 5, sufficient diketal 6 to necessitate expensive and laborious bisulfite separation and recyclization steps. It has now been found unexpectedly that the separation and recyclization steps of the prior process can be voided by the selective ketalization of the 6-keto group of a 3-alkoxycarbonylalkan-2,6-dione of formula 9 to a 3-alkoxycarbonyl-6,6-alkylenedioxyalkan-2-one of formula 10 in sufficient purity to be useful in the subsequent steps of the instant process without a further bisulfite purfication.

The selective ketalization of 3-alkoxycarbonylalkan-2,6-diones of formula 9 is performed by treatment with an alkylene glycol of formula 13 wherein $R_1$ and $R_2$ are hydrogen or lower alkyl and n is 0 to 2 in a suitable inert organic solvent containing an acid-catalyst at a reaction temperature of about 0° to about 30°C to afford 3-alkoxycarbonyl-6,6-alkylenedioxyalkan-2-ones of formula 10. Suitable inert organic solvents include, for example, aromatic solvents, such as benzene, toluene, xylene and the like. Benzene is the preferred solvent for the selective ketalization step.

Among the acid-catalysts which have been found to be useful in the ketalization step are sulfuric acid and lower alkyl and aromatic sulfonic acid derivatives thereof, such as methanesulfonic acid, benzenesulfonic acid, p-toluenesulfonic acid and the like. Sulfuric acid is the preferred acid catalyst.

While reaction temperatures within the range of about 0° to about 30°C are not critical, reaction temperatures above 30°C in the ketalization step are to be avoided to suppress undesired diketal formation. A reaction temperature of about 0°C is preferred.

The final step of the process of the present invention for the preparation of 6,6-alkylenedioxyalkan-2-ones of formula 11 involves alkaline hydrolysis of the alkoxycarbonyl group of compounds of formula 10, followed by acidification and decarboxylation of the resultant unstable beta-ketoacid of formula 10 wherein $R_1$, $R_2$ and $n$ are as hereinbefore defined and $R_3$ is hydrogen. This step of the process is performed by treatment of beta-ketoesters of formula 10 with an aqueous solution of an alkali metal hydroxide, such as sodium or potassium hydroxide, to form the alkali metal salts of the beta-ketoacid of formula 10 wherein $R_1$, $R_2$ and $n$ are as hereinbefore defined and $R_3$ is an alkali metal, which are then treated with a suitable acid and an inert solvent, and finally heated at about 50° to about 100°C for about 30 minutes to about 1 hour to complete the decarboxylation.

Suitable inert solvents for the acidification of the alkali metal salts of the beta-ketoesters of formula 10 are water, lower alkanols and mixtures thereof. Water is the preferred inert solvent.

Acids suitable for the acidification of the alkali metal salts of the beta-ketoesters in the final step of the process of the present invention include weak organic aliphatic and aromatic acids, such as carbonic, acetic, propionic, oxalic, malonic, fumaric, citric, benzoic, phthalic, naphthanoic and the like, and weak inorganic acids, such as phosphorous, sulfurous, boric and the like. Carbonic acid is preferred. The reaction temperature necessary to complete the decarboxylation is not critical. The decarboxylation proceeds at a convenient rate between temperatures of about 50° to about 100°C and at a most convenient rate at steam bath temperatures. The decarboxylation time, on the other hand, is critical. Decarboxylation times of about 1 hour are preferred. The yield of the 6,6-alkylenedioxyalkan-2-ones of formula 11 decreases rapidly with longer reaction times.

While acidification of alkali metal salts of the beta-ketoacids of formula 10 promotes the decarboxylation of the salts, it is not necessary for the practice of the invention. Heating aqueous solutions of the salts within the afore-mentioned temperature range also results in decarboxylation to the monoketals of formula 11. As in the case of acidification, the decarboxylation time appears to be critical. Decarboxylation times greater than about 1 hour give rise to reduced yields and are to be avoided.

While the process of the present invention for the preparation of 6,6-alkylenedioxyalkan-2-ones may be carried out stepwise as delineated in the Reaction Scheme and immediately preceding description, the process is advantageously performed on a commercial scale without isolation of the intermediate 3-alkoxycarbonylalkan-2,6-diones and 3-alkoxycarbonyl-6,6-alkylenedioxyalkan-2-ones of formulas 9 and 10, respectively, i.e., as a one-pot process. This process not only enjoys all of the economic and practical advantages inherently associated with a one-vessel process, but as already stressed, obviates the uneconomical and inconvenient bisulfite purification step of the prior process described in U.S. Pat. No. 3,767,677.

The 3-alkoxycarbonyl-6,6-alkylenedioxyalkan-2-ones of formula 10 of the present invention are useful as intermediates for the preparation of 6,6-alkylenedioxyalkan-2-ones of formula 11, which in turn are useful for the preparation of 1-alkoxycarbonyl-6,6-alkylenedioxyalkan-2-ones of formula 12. The beta-ketoesters of formula 12 are employed as intermediates in the total synthesis of steroids having therapeutically valuable properties.

EXAMPLES

The following examples are for illustrative purposes only and are not to be construed as limiting the invention described herein in any way whatsoever.

EXAMPLE 1

Preparation of
5-(2-Methyl-1,3-dioxolan-2-yl)-2-pentanone (11, R, $R_1$, $R_2$ are hydrogen and n is 0)

Methyl vinyl ketone (freshly distilled and stabilized with a trace of hydroquinone, 70 g, 1.0 mole) was added dropwise to a stirred solution of ethyl acetoacetate (130 g, 1.0 mole) and sodium ethoxide and absolute ethanol, prepared from sodium (0.5 g, 22 mmoles) and absolute ethanol (10 ml) 20°–25°C over a 30-minute period. After stirring at room temperature for 30 minutes, the reaction mixture was cooled in an ice bath and benzene (800 ml), ethylene glycol (800 g, 12.8 moles) and conc. sulfuric acid (96–98%, 15 ml) was added. The reaction mixture was stirred at the ice-bath temperature overnight. The layer was separated and the lower layer was extracted with benzene. The benzene extract was combined with the upper benzene layer of the reaction mixture and a solution of sodium hydroxide (42 g, 1.05 moles) in water (750 ml) was added to the combined benzene extracts, and the two-phase system was stirred vigorously at room temperature for 2 hours. The layers were separated and a fresh solution of sodium hydroxide (20 g, two-phase mole) was added to the benzene layer. The two-phase system was stirred vigorously at room temperature for 2 hours and the layers were separated. Finely crushed dry ice (80 g) was added to the combined aqueous phases and the solution was heated on a steam bath for 1 hour with stirring. The mixture was allowed to cool to room temperature and, after the addition of sodium chloride (100 g), was extracted with benzene (3 × 300 ml). The combined extracts were dried over anhydrous sodium sulfate. The drying agent was removed by filtration and the filtrate was concentrated under reduced pressure. Distillation of the residual oil gave 106 g (61%) of the alkylenedioxyalkanone as a colorless oil, boiling point 73°–78°C (0.15 mm).

The purity (98%) of the product was established by gas-liquid chromatographic analysis.

EXAMPLE 2

Preparation on
5-(2-Ethyl-1,3-dioxolan-2-yl)-2-pentanone (11, R is methyl, $R_1$ and $R_2$ are hydrogen and n is 0)

Ethyl vinyl ketone (11.4 g, 0.136 mole) was added dropwise over 75 minutes to a solution of ethyl acetoacetate (17.6 g, 0.112 mole) and 20% sodium ethoxide in ethanol (1.35 ml), cooled to 20°C. The reaction mixture was stirred at room temperature for 30 minutes. Benzene (120 ml), ethylene glycol (120 g, 1.9 moles) and conc. sulfuric acid (2.25 ml) were added consecutively to the reaction mixture maintained at 0°C by external cooling. The mixture was stirred at 0°C overnight. The layers were separated and the glycol layer was extracted with benzene (75 ml). The combined benzene layers were stirred with 2.6% aqueous sodium hydroxide solution (310 ml) overnight at room temperature. The layers were separated and the aqueous phase was treated with dry ice (12 g) and the solution was heated at 85°C for 1 hour. The solution was allowed to cool to room temperature, sodium chloride (15 g) was added and the solution was extracted with benzene (3 × 150 ml). The combined benzene extracts were dried over anhydrous sodium sulfate, the drying agent was collected on a filter and the filtrate was concentrated under reduced pressure. Distillation of the residual oil gave 12.7 g (50%) of the monoketal as a colorless oil, boiling point 63°–65 °C (0.15 mm).

EXAMPLE 3

Preparation of 5-(2,4-Dimethyl-1,3-dioxolan-2-yl)-2-pentanone (11, R and $R_1$ are hydrogen, $R_2$ is methyl and n is 0)

Methyl vinyl ketone (7.0 g, 0.100 mole) was added dropwise over 1 hour to a mixture of ethyl acetoacetate (13.0 g, 0.101 mole) and 20% sodium ethoxide in ethanol (1 ml), cooled to 20°C. The reaction mixture was stirred at room temperature for 30 minutes. Benzene (80 ml) and propylene glycol (99 g, 1.30 moles) were added consecutively. The two-phase system was cooled to 0°C, conc. sulfuric acid (1.5 ml) was added and the solution was stirred at 0°C for 2 hours. The layers were separated and the glycol layer was extracted with benzene. Aqueous sodium hydroxide solution (2%, 200 ml) was added to the combined benzene extracts and the mixture was stirred at room temperature overnight. The layers were separated and an additional 100 ml of 2% aqueous sodium hydroxide solution was added to the benzene layer. The two-phase system was stirred at room temperature for 1 hour and the layers were separated. Dry ice (9 g) was added to the combined aqueous phases and the solution was heated at 85°C for 1 hour. The solution was allowed to cool to room temperature, sodium chloride (15 g) was added and the solution was extracted with benzene (3 × 100 ml). The combined organic extracts were dried over anhydrous sodium sulfate, the drying agent was collected on a filter and the filtrate was concentrated under reduced pressure. Distillation of the residue gave 9.2 g (49%) of the monoketal as a colorless oil, boiling point 57°–61°C (0.15 mm).

We claim:

1. A process for the preparation of a 6,6-alkylenedioxyalkan-2-one of the formula

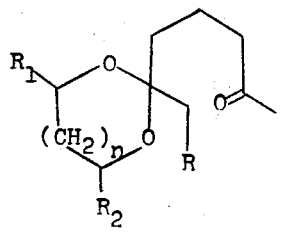

wherein R, $R_1$ and $R_2$ are hydrogen or lower alkyl and n is 0, 1 or 2 which comprises the steps of:
 a. treating a compound of the formula

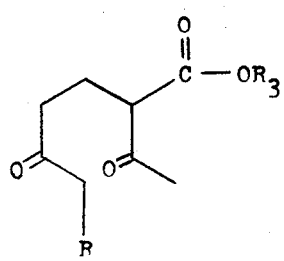

wherein $R_3$ is lower alkyl with an alkylene glycol of the formula

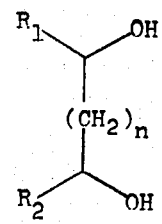

wherein $R_1$ and $R_2$ are as defined above in reaction system comprising an acid-catalyst selected from the group consisting of sulfuric acid and lower alkyl and aromatic sulfonic acids, and an aromatic solvent to form a delta-alkylenedioxy-beta-ketoester of the formula

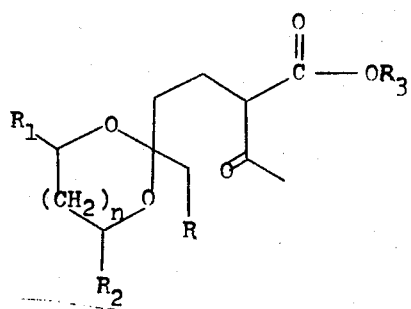

wherein R, $R_1$, $R_2$, $R_3$ and n are as defined above;
 b. treating the delta-alkylenedioxy-beta-ketoester with an aqueous solution of an alkali metal hydroxide; and
 c. treating the aqueous solution with acid.

2. The process of claim 1 wherein the acid-catalyst is sulfuric acid.

3. The process of claim 1 wherein R, $R_1$ and $R_2$ are hydrogen and $n$ is 0.

4. The process of claim 1 wherein R is methyl, $R_1$ and $R_2$ are hydrogen an $n$ is 0.

5. The process of claim 1 wherein R and $R_1$ are hydrogen, $R_2$ is methyl and $n$ is 0.

6. The process of claim 1 wherein the aromatic solvent is benzene.

7. The process of claim 1 wherein the alkali metal hydroxide is sodium hydroxide.

8. The process of claim 1 wherein the acid is a mild acid.

9. The process of claim 8 wherein the mild acid is dry ice.

10. The process of claim 1 wherein said process is performed in one reaction vessel without isolation of the intermediates.

11. A compound of the formula

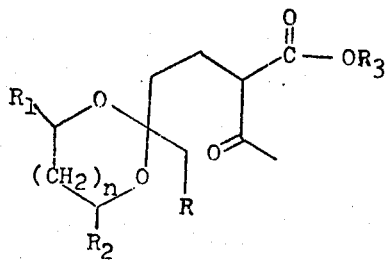

wherein R, $R_1$, and $R_2$ are hydrogen or lower alkyl, $R_3$ is lower alkyl and $n$ is 0, 1 or 2.

12. A compound according to claim 11 wherein R and $R_2$ are hydrogen or lower alkyl, $R_1$ is hydrogen, $R_3$ is lower alkyl and $n$ is 0.

13. A compound according to claim 12 wherein R, $R_1$ and $R_2$ are hydrogen, $R_3$ is ethyl and $n$ is 0.

14. A compound according to claim 13 wherein R is methyl, $R_1$ and $R_2$ are hydrogen, $R_3$ is ethyl and $n$ is 0.

15. A compound according to claim 13 wherein R and $R_1$ are hydrogen, $R_2$ is methyl, $R_3$ is ethyl and $n$ is 0.

* * * * *

UNITED STATES PATENT AND TRADEMARK OFFICE
CERTIFICATE OF CORRECTION

PATENT NO. : 3,972,898
DATED : August 3, 1976
INVENTOR(S) : Urs Oskar Hengartner and Pius Anton Wehrli It is certified that error appears in the above-identified patent and that said Letters Patent are hereby corrected as shown below:

Column 8, claim 1, line 12, "in reaction" should be in a reaction.

Column 9, claim 11, line 2, "n is 0, 1 or 2" should be n is 0.

Signed and Sealed this

Twelfth Day of August 1980

[SEAL]

Attest:

SIDNEY A. DIAMOND

Attesting Officer

Commissioner of Patents and Trademarks